US006363772B1

(12) United States Patent
Berry

(10) Patent No.: US 6,363,772 B1
(45) Date of Patent: Apr. 2, 2002

(54) SYSTEM AND METHOD FOR DETECTION OF A BIOLOGICAL CONDITION

(75) Inventor: Michael J. Berry, Carmel, CA (US)

(73) Assignee: Quadrivium, L.L.C., Phoenix, AZ (US)

( * ) Notice: Subject to any disclaimer, the term of this patent is extended or adjusted under 35 U.S.C. 154(b) by 0 days.

(21) Appl. No.: 09/459,251

(22) Filed: Dec. 10, 1999

(51) Int. Cl.[7] .......................... G01N 23/00; G01N 21/00
(52) U.S. Cl. ................ 73/24.02; 73/24.01; 73/24.06; 73/30.04; 73/31.05; 250/339.13; 356/437
(58) Field of Search ................ 436/164; 250/227.24, 250/343, 339.13; 73/24.02, 61.49, 24.01, 24.06, 30.04, 31.05; 356/432, 437

(56) References Cited

U.S. PATENT DOCUMENTS

| | | | |
|---|---|---|---|
| 3,792,272 A | * | 2/1974 | Harte et al. ................ 250/343 |
| 3,820,901 A | | 6/1974 | Kreuzer ....................... 356/97 |
| 3,893,771 A | | 7/1975 | Bell ............................. 356/97 |
| 4,197,009 A | | 4/1980 | Berry et al. ................ 356/301 |
| 4,269,509 A | | 5/1981 | Berry et al. ................ 356/301 |
| 4,534,360 A | | 8/1985 | Williams ..................... 128/665 |
| 4,740,086 A | * | 4/1988 | Oehler et al. .............. 356/432 |
| 4,772,559 A | | 9/1988 | Preti et al. .................... 436/64 |
| 5,339,674 A | * | 8/1994 | Hammerich et al. ....... 73/24.02 |
| 5,348,002 A | | 9/1994 | Caro ............................ 128/633 |
| 5,450,193 A | | 9/1995 | Carlsen et al. ............. 356/301 |
| 5,465,728 A | | 11/1995 | Phillips ....................... 128/730 |
| 5,625,189 A | | 4/1997 | McCaul et al. ............. 250/343 |
| 5,753,285 A | | 5/1998 | Horan .......................... 426/87 |
| 5,933,245 A | * | 8/1999 | Wood et al. ................ 356/437 |
| 5,996,586 A | | 12/1999 | Phillips ....................... 128/898 |
| 6,108,096 A | * | 8/2000 | Ushio et al. ................ 356/432 |
| 6,160,255 A | * | 12/2000 | Sausa ..................... 250/227.24 |
| 6,161,426 A | * | 12/2000 | Byatt et al. ................ 73/61.49 |
| 6,202,470 B1 | * | 3/2001 | Chou ........................... 73/24.02 |

FOREIGN PATENT DOCUMENTS

DE 19522774 1/1997

OTHER PUBLICATIONS

B. Krotoszynski et al., "Characterization of Human Expired Air: A Promising Investigative and Diagnostic Technique", pp. 239–244, Journal of Chromatographic Science, vol. 15, Jul. 1977.

S.M. Gordon et al., "Volatile Compounds In Exhaled Air From Patients With Lung Cancer", pp. 1278–1282, Clinical Chemistry, vol. 31, No. 8, 1985.

S. Bernegger et al., "Longitudinal Resonant Spectrophone for Co–Laser Photoacoustic Spectroscopy", pp. 125–132; Applied Physics, B44, 1987.

H.J. O'Neill et al., "A Computerized Classification Technique For Screening For The Presence Of Breath Biomarkers In Lung Cancer", pp. 1613–1618, Clinical Chemistry, vol. 34, No. 8, 1988.

Mitsui et al., "Clinical Chemistry", pp. 1993–1995, vol. 43, No. 10, 1997.

* cited by examiner

Primary Examiner—Jill Warden
Assistant Examiner—Brian J. Sines
(74) Attorney, Agent, or Firm—Fletcher, Yoder & Van Someren

(57) ABSTRACT

A system and method that allows for early detection of biological conditions, such as a disease, through analysis of appropriate gaseous samples. The system and method are particularly amenable to the early screening for diseases, such as lung cancer, through the detection of specific biomarkers when present in exhaled breath from an individual. A preferred system implements a CO overtone laser that generates radiation and directs it through a photoacoustic cell. The absorption of the radiation is detected acoustically, and the absorption characteristics are utilized in determining the presence of a specific biological condition.

12 Claims, 7 Drawing Sheets

SYSTEM AND METHOD FOR DETECTION OF A BIOLOGICAL CONDITION

FIELD OF THE INVENTION

The present invention relates generally to the detection of volatile organic compounds that serve as biomarkers for a biological condition, such as a disease, and particularly to a noninvasive system and method for determining the presence of such condition in an individual or substance through analysis of a gaseous sample from the individual or substance.

BACKGROUND OF THE INVENTION

Early detection of disease in an individual is often important to successful treatment of that disease. A variety of techniques are used to test for specific diseases either before or after symptoms occur. For example, blood samples and urine samples are routinely taken for analysis and detection of abnormalities indicative of disease. Many of these techniques are invasive or uncomfortable for the patient.

One potential noninvasive technique for determining the presence of a variety of diseases in the body of an individual is breath analysis. There are over three hundred distinct chemical compounds that may be detected in human expired breath, and each of these distinct chemical compounds has its own absorption spectrum. Studies have shown that specific alterations or changes in this expired air are indicative of specific diseases. This is true for some diseases because of the direct compositional relationship between constituents carried in the blood stream and constituents excreted into the alveolar spaces of the lungs. In any event, the changes or alterations in the constituents of an individual's breath can be detected to determine whether the individual has a particular biological condition, such as a disease or metabolic disorder.

The presence of a given disease can be indicated by the addition or absence of one or more constituents in a gaseous sample (e.g., expired air) otherwise not present, a change in concentration of one or more constituents or a combination of the two. Thus, a successful diagnostic technique must be able to readily detect the addition or change in concentration of constituents. The addition of a constituent and/or the change in concentration of a constituent are often referred to as biochemical markers or biomarkers. Detection of biomarkers has been a complex task due to the large number of constituents within human expired air and due to the constant change of constituents that results from environmental pollutants and other components which enter an individual's lungs.

To the present, analysis of human expired air largely has been accomplished by using gas chromatography/mass spectrometry which detects the numerous components within human-expired air. The use of a gas chromatographic/mass spectrometric technique has been necessary because of the number of constituents and because of their presence in submicrogram per liter to microgram per liter concentrations. Various statistical analyses are performed on the results with the aid of a personal computer to determine the presence of biomarkers. This technique, however, is expensive and time consuming, rendering it inappropriate for the routine testing of individuals.

The gas chromatography/mass spectrometry technique has been used in researching biomarkers associated with lung cancer. Lung cancer is a disease of particular interest due to its growing presence, severe effects and difficulty of early detection. Diagnostic techniques that have been used in the past to detect pre-symptomatic lung cancer include chest x-rays, fiber optic bronchoscopy and sputum cytology. However, these techniques are costly to administer and have not been adopted as standard screening techniques. Like the gas chromatography/mass spectrometry approach, these techniques are not amenable to large-scale use for early detection of lung cancer.

Similar problems are involved in detecting other biological conditions. For example, biomarkers contained in the gases resulting from metabolic activity in cell cultures, pathology specimens or food specimens may contain biomarkers indicative of a biological condition, such as disease, spoilage or other contamination. Photoacoustic detection has been used to determine VOCs present in certain of these types of gaseous samples, but it has been limited in its application to breath samples, due to, for example, the moisture content of breath. Water vapor tends to have high absorbance of the laser energy used in conventional photoacoustic detection across a broad spectrum.

It would be advantageous to have a quick inexpensive system and method for analyzing gaseous samples, such as the exhaled breath of an individual or the gases proximate cell cultures, pathology specimens, food specimens, etc., to determine detrimental biological conditions, such as spoilage or diseases, e.g., lung cancer, renal failure, liver disease and diabetes, for which specific biomarkers are present in human expired air.

SUMMARY OF THE INVENTION

The present invention features a system and method for detecting at least one specific volatile organic compound in a gaseous sample. The specific volatile organic compound is indicative of a biological condition when present in a given amount. The method includes obtaining a gaseous sample that has been exposed to or is suspected of being exposed to byproducts of a biological agent. A CO overtone laser is operated in a vibrational overtone sequence to generate a radiation that undergoes a characteristic intense absorption by the at least one specific volatile organic compound. The radiation is directed into the sample, and any characteristic intense absorption is detected. This provides an indication of whether the biological condition exists, based on the presence and amount of the at least one specific volatile organic compound.

According to another aspect of the invention, a system is provided for detecting a biomarker indicative of the presence of a biological condition. The system comprises a photoacoustic cell having an inlet through which a gaseous sample may be introduced into an interior of the photoacoustic cell. An overtone laser is combined with the photoacoustic cell and positioned to direct a radiation through the photoacoustic cell. The selected radiation is of a frequency predetermined for a characteristic intense absorption by at least one specific biomarker contained in the gaseous sample. The system also includes a detector coupled to the photoacoustic cell to detect the characteristic intense absorption indicative of the at least one specific biomarker.

According to another aspect of the invention, a method for detecting whether a given biomarker is present in the selected gaseous sample is disclosed. The method includes obtaining a gaseous sample and selecting a radiation in the form of an overtone laser transition occurring at a frequency such that the radiation undergoes a characteristic absorption by a given biomarker if present in the gaseous sample. The method further includes directing the radiation into the gaseous sample, and detecting whether the characteristic absorption occurs.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENTS

Figure 1:
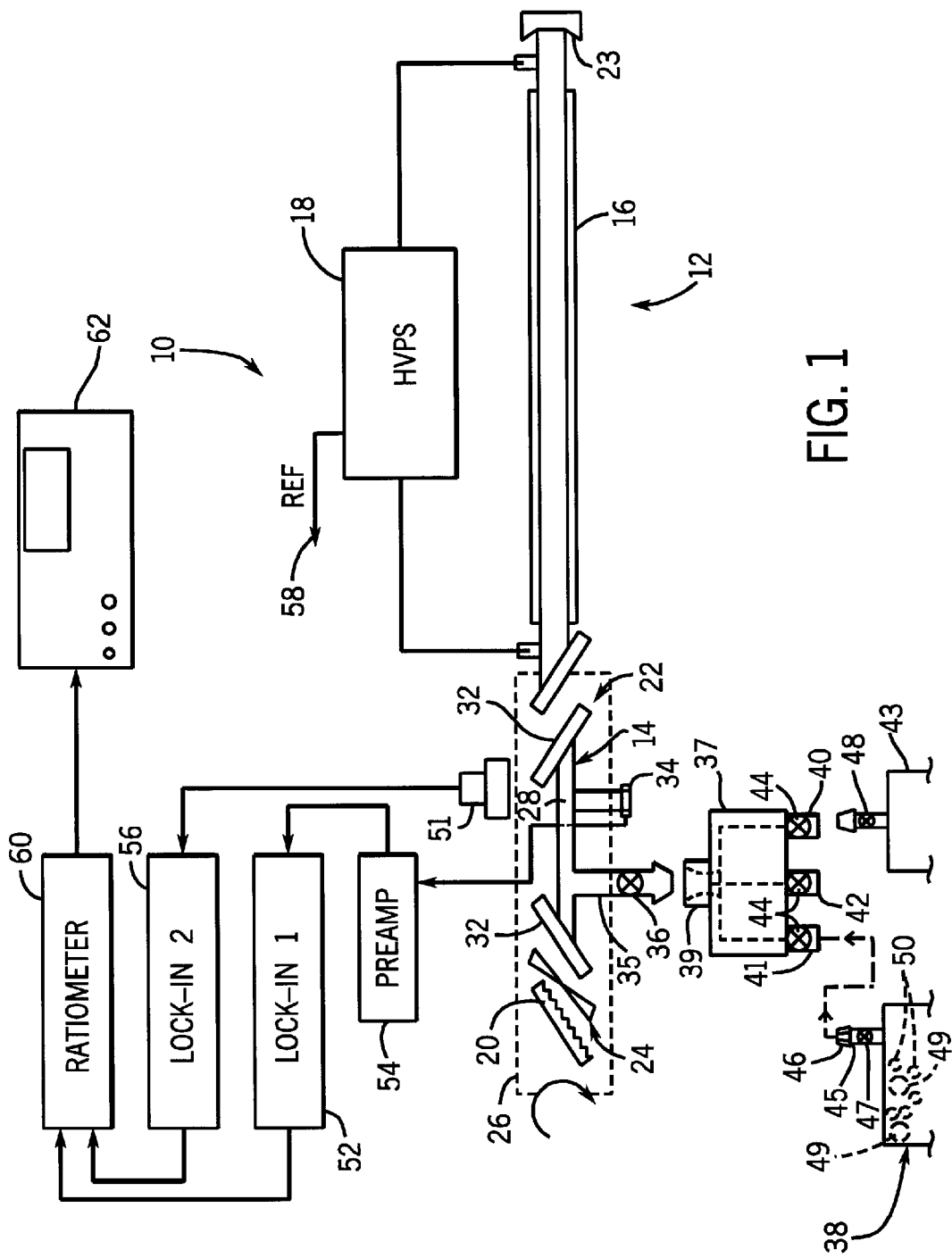
FIG. 1 is a schematic illustration of a photoacoustic system according to a preferred embodiment of the present invention.

The present invention includes a system and method for detecting biological conditions through noninvasive analysis of gaseous samples. The focus of the following exemplary description is on the detection of biomarkers that are indicative of lung cancer within an individual. However, this system and method can be modified to detect a biomarker(s) in an individual's exhaled breath indicative of other diseases, such as renal failure, liver disease or diabetes. Further, the system and method can be utilized to detect biomarkers expelled into the environment proximate cell cultures, pathology specimens, food specimens, etc., where metabolic processes occur. For example, the system and method can be used for food inspection at a processing facility to insure that the food products have not been contaminated by decay or other infestation of undesirable aerobic or anaerobic organisms. Such organisms undergo metabolic processes that release carbon dioxide or ammonia that can be detected via the present inventive system and method.

Generally, the present system and method utilize photoacoustic detection to determine whether there exist certain biomarkers within a subject gaseous sample. Biomarkers are individual constituents, combinations of constituents at given concentrations or the entire group of volatile organic compounds (VOCs) found in a sample that can be compared to a reference sample. For example, VOCs within exhaled breath can indicate a substantial likelihood of the presence of lung cancer (or other biological condition) in the individual or substance being tested.

Examples of constituents within exhaled breath that are indicative of lung cancer include e-caprolactone ($C_6H_{10}O_2$), 2-butanone and acetone. Studies have shown that the presence of c-caprolactone in the exhaled breath of an individual indicates a ninety percent likelihood that the individual has lung cancer. Similarly, the presence of 2-butanone and the presence of acetone at given concentration levels also provide a strong indication of the presence of lung cancer within the individual. Thus, the presence of these constituents at a given concentration level in the individual's expired air provides an indication of lung cancer. The individual constituents or the collective VOCs in a breath sample can serve as a biomarker for lung cancer. The present invention provides a relatively simple, quick and inexpensive system and method for determining the presence of such biomarkers to allow for early screening of lung cancer.

According to a preferred embodiment of the present invention, the pertinent biomarkers can be determined via photoacoustic detection. Generally, a radiation generating source, such as a laser, is used to generate a radiation that may be directed into a gaseous sample, e.g., exhaled breath from a subject or substance being tested. Preferably, the laser is a carbon monoxide overtone laser tuned to a selected wavelength or wavelengths. The biomarkers of interest are known to have infrared absorption spectra, and therefore the wavelength or wavelengths of the radiation is selected from within a specific band of infrared wavelengths. carbon monoxide lasers utilized in the fundamental spectral region ($\Delta v=-1$) can be used in certain situations to detect biomarkers of interest. However, it has been discovered that use of an overtone laser, specifically a carbon monoxide (CO) overtone laser can be advantageous. For example, breath samples and other samples can be analyzed without removal of water vapor that tends to interfere with analysis in some desired spectral regions using CO $\Delta v=-1$ transitions. Additionally, the overtone laser provides more universal detection of volatile organic compounds that serve as biomarkers. For example, all volatile organic compounds present in breath can be detected in the CO overtone laser spectra region because such VOCs have carbon-hydrogen (CH) stretch absorptions in this region. In fact, the CO overtone laser enables the detection of every VOC having a CH, NH and OH bond because each has absorption features detectable within the CO overtone laser spectral region.

Although a variety of overtone lasers can be utilized and potentially operated in the $\Delta v=-2$, $\Delta v=-3$, $\Delta v=-4$, etc. bands, it is preferred that CO $\Delta v=-2$ laser transitions are utilized in the present laser photoacoustic detection. Additionally, the CO overtone laser typically uses one or more bands of $^{12}C^{16}O$ overtone ($\Delta v=-2$) laser transitions, but other isotopic variants potentially can be used to obtain appropriate characteristic absorptions. For example, $^{13}C^{16}O$ and $^{12}C^{18}O$ are isotopic modifications that may work well in detecting certain VOCs within certain spectral regions.

In testing for a biological condition, a gaseous test sample is placed inside a photoacoustic cell, and radiation is directed through the cell. A microphone is connected to the photoacoustic cell and exposed to the gaseous sample therein. The microphone is able to detect absorption of the radiation by a specific biomarker via pressure changes within the photoacoustic cell. For example, the overtone laser described above maybe tuned to generate radiation having a wave number that corresponds to a potential characteristic intense absorption different from the absorption that would occur without the subject biomarker.

Preferably, the radiation from the laser is chopped at a certain frequency, thereby producing a corresponding modulation of absorption of the radiation by the gaseous sample within the photoacoustic cell. Assuming the appropriate biomarker is present, the absorption of radiation by the biomarker results in a heating of the biomarker gas that generates an acoustic wave detectable by the microphone. An acoustic signal enhancer, such as helium, can be added to the sample of breath being tested to facilitate generation of this acoustic wave.

Referring now to FIG. 1, a photoacoustic detection system 10, according to a preferred embodiment of the present invention, is schematically illustrated. Although this is a preferred embodiment, a variety of component arrangements and modifications may be made without departing from the scope of the invention. In the illustrated embodiment, an electromagnetic radiation generator or radiation source 12 is used to generate a desired radiation having a wavelength or wavelengths that will be characteristically absorbed by a specific biomarker or biomarkers, if present within the gaseous sample being analyzed. The sample is contained within a photoacoustic cell 14 during the analysis.

In the preferred embodiment, radiation source 12 is a continuous wave (CW), grating-tuned carbon monoxide (CO) overtone laser 16 connected to a high voltage power supply 18. Overtone laser 16 operates on one or more selected transitions of $^{12}C^{16}O$ and/or other isotopic variants (e.g. $^{13}C^{16}O$ or $^{12}C^{18}O$) of carbon monoxide depending on a given biomarker's absorption spectrum and the location of its characteristic intense absorption within that spectrum. A preferred exemplary laser is a cw CO overtone laser operating in the 2.6 to 4.0 $\mu$m spectral region. A specific procedure utilizes CO overtone laser transitions that occur in the 2.6 to 4.0 $\mu$m spectral region based on the $\Delta v=-2$ vibrational band sequence, such as the V=13→11, 12→10, etc. vibrational bands. Use of this spectral region helps avoid spectral interference from water vapor and other contaminants in potentially determining a wider variety of VOCs that may be present in the gaseous sample, e.g., breath sample, cell culture sample, food specimen sample, etc.

The laser transitions are tuned by a diffraction grating 20 that is typically mounted on a rotation stage (not shown) as is understood by those of ordinary skill in the art. The laser 16 is modulated either by voltage modulation of its high voltage power supply 18 or by a mechanical chopper 24, preferably disposed with an optical cavity 22. Optical cavity 22 is located between a cavity mirror 23 of laser 16 and diffraction grating 20.

Although photoacoustic cell 14 can be disposed outside optical cavity 22, it preferably is located within optical cavity 22 to use the intracavity power of the individual laser lines. Correspondingly, this intracavity placement of the photoacoustic cell will increase the detection sensitivity of photoacoustic detection system 10, often by a factor of 100 or more. In the illustrated embodiment, a purge box 26 (shown by dashed lines) encloses photoacoustic cell 14, diffraction grating 20, chopper 24 (if used) and the end of laser 16 proximate photoacoustic cell 14.

Figure 2:
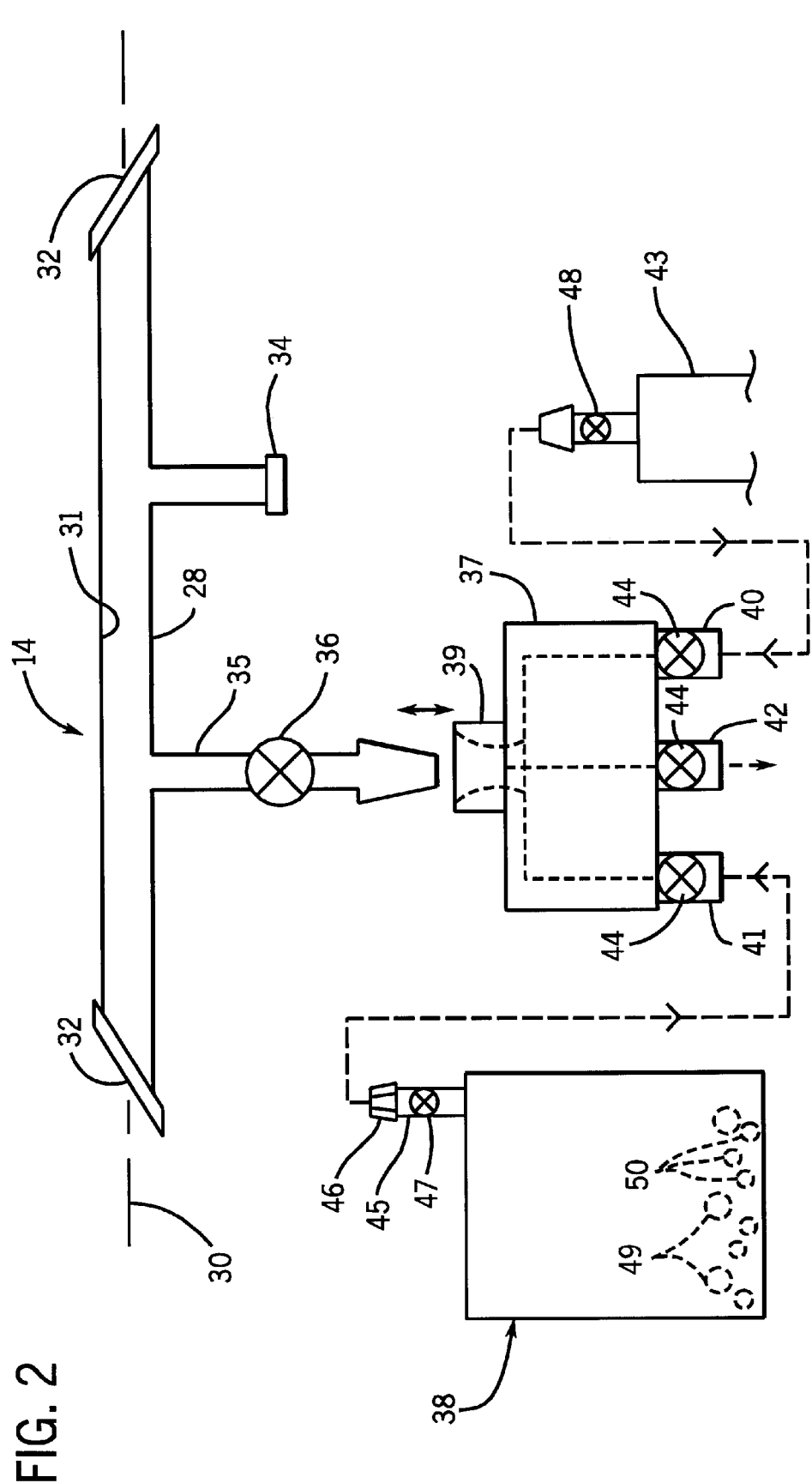
FIG. 2 is a schematic illustration of a photoacoustic cell that can be used in the system illustrated in FIG. 1.

Photoacoustic cell 14 can be designed in a variety of configurations to optimize its effectiveness. In a preferred exemplary embodiment, photoacoustic cell 14 includes a generally linear body 28 that lies along an axis 30 (see FIG. 2). Linear body 28 preferably has a hollow interior 31 that is generally cylindrical in cross section. A pair of cell windows 32, such as ZnSe windows, are mounted to linear body 28 with one window 32 at each end. Preferably, cell windows 32 are each mounted at Brewster's angle to reduce intracavity losses. Additionally, a microphone 34, such as an electret microphone, is coupled to photoacoustic cell 14 and exposed to its interior cavity 31 as well as any samples of breath introduced therein. An exemplary microphone is a Knowles Electronics BT-1759 electret microphone.

An inlet/outlet port 35 is connected to linear body 28 to permit the gaseous sample, e.g., expired breath, to be introduced into interior cavity 31 and removed therefrom. Additionally, it may be desirable to introduce an acoustic signal enhancer, such as helium, into interior cavity 31. Additionally, it may be desirable to introduce a calibration gas, such as $SF_6$, into interior cavity 31. Potentially, both the gaseous sample and helium can be introduced into photoacoustic cell 14 through port 35.

Port 35 includes a valve 36 that allows the ingress of the gaseous sample (and, if used, the acoustic signal enhancer) but not its egress during analysis. Following analysis of the sample, valve 36 is opened and the sample is extracted or sucked from interior cavity 31. After removal of the sample, valve 36 is shut to retain a vacuum within interior cavity 31. This lower pressure allows the next gaseous sample to be expanded into photoacoustic cell 14 via the higher outside pressure that forces the sample into the lower pressure or vacuum within interior cavity 31.

In the illustrated embodiment, port 35 is designed for coupling to a manifold 37 which, in turn, is designed for coupling to a sample container 38. Sample container 38 may comprise a variety of configurations, such as a preevacuated flexible bag that can be filled with the desired gaseous sample within a sample collection container used to collect exhaled breath or the gases proximate other biological agents, e.g., cell cultures, pathology specimens or food specimens, that potentially have been exposed to byproducts of the metabolism of the biological agent. In the case of breath analysis, the individual (biological agent) potentially can exhale directly into the flexible bag to provide the sample for analysis. The container 38 preferably includes a valve port to permit entry of the sample and prevent any leakage or unwanted contamination.

Manifold 37 includes a connection port 39, designed for mating engagement with port 35. Manifold 37 also includes a helium port 40, a sample port 41 and an evacuation port 42. A helium supply 43 (see FIG. 2) may be attached to helium port 40; sample container 38 may be attached to sample port 41; and vacuum pump (not shown) may be attached to evacuation port 42. A valve 44 is disposed in each port 40 and 41 to permit inflow of the helium and the breath sample. A similar valve 44 is disposed in evacuation port 42 to facilitate evacuation of manifold 37, interior cavity 31 and the "dead space" between valves.

Sample container 38 includes an outlet port 45 designed for sealing engagement with sample port 41 of manifold 37. Outlet port 45 can also serve as the port through which the sample is admitted into container 38, or a separate inlet port can be provide depending on the specific application. In one embodiment, outlet port 45 includes a contoured surface 46, such as a tapered octagonal or hexagonal surface that is designed for mating engagement with a corresponding contoured surface of sample port 41. This will help ensure that only the desired sample container 38 is connected to manifold 37 and ultimately photoacoustic cell 14. After making the connections, the sample of breath can be expanded or otherwise forced into interior cavity 31 of photoacoustic cell 14. In lieu of a single inlet/outlet port 35, photoacoustic cell potentially can be designed with separate inlet and outlet ports connected to body 28.

In the preferred embodiment, sample container 38 includes a valve 47 disposed in outlet port 45. Similarly, the helium supply 43 includes a valve 48. This permits a sample of breath to be introduced into interior cavity 31 of photoacoustic cell 14 as follows: Manifold 37 is connected to port 35 of photoacoustic cell 14 via connection port 39. Sample container 38, with valve 47 closed, is connected to sample port 41 via outlet port 45, helium supply 42, with valve 48 closed, is connected to helium port 40, and a vacuum is applied at evacuation port 42. Valves 47 and 48 remain closed, and valve 36 as well as valves 44 are opened to evacuate interior cavity 31 and manifold 37 via the vacuum applied at evacuation port 42.

After evacuation, valve 44 of evacuation port 42 is closed, and valve 47 of sample container 38 is opened to permit expansion of the gaseous sample into interior cavity 31 of photoacoustic cell 14. Valve 47 may then be closed and valve 48 opened to permit the flow of helium into interior cavity 31. Generally, the helium is at a higher pressure than the gaseous sample, so it will readily flow into photoacoustic cell 14. A pressure gauge (not shown) may be connected to manifold 37 for monitoring both the sample pressure and the helium pressure to facilitate preparation of reproducible and/or optimized mixtures in interior cavity 31. Of course, the exact method for handling and testing the gaseous sample may vary depending on the type of photoacoustic cell and/or manifold that is used and whether an acoustic signal enhancer, such as helium, and/or a calibration gas, such as $SF_6$, is combined with the sample.

When the gaseous sample is a breath sample, such as when searching for a lung cancer biomarker, it may be desirable to use a pure breathing gas to "wash out" contaminants from the lungs prior to collecting a breath sample. An exemplary breathing gas is heliox, which is commonly mixed 80% helium and 20% oxygen by volume. In obtaining the breath sample, the heliox mixture typically is inhaled and exhaled several times prior to exhaling of the breath sample. The heliox provides the breath sample with helium that acts as a signal enhancer for laser photoacoustic detection. Potentially, the introduction of helium into photoacoustic cell 14 through valve 48 can be omitted.

Heliox also is desirable as a wash out gas because lungs have relatively low pulmonary resistance to heliox compared to ordinary air. Thus, the heliox permits washing and sampling of the most distal alveolae within the lungs. This permits the detection of VOCs produced by such distal alveolae, which can be important in the diagnosis of certain types of lung cancer, such as adenocarcinoma.

The heliox mixture also may contain sulfur hexafluoride ($SF_6$), which is an inert gas having a characteristic intense infrared absorption peak at ca. 947 $cm^{-1}$ which is not readily absorbed by bronchial epithelial cells. $SF_6$ therefore can be used as an "internal standard" in breathing gas mixtures to quantitate the amount of expired breath and to assure the integrity of the breath collection procedure and sample. Incorporation of trace amounts (less than approximately 0.1% by volume) of $SF_6$ is sufficient to gain the benefits of this internal calibration standard.

Heliox also is beneficial in removing water vapor from the breath sample. Although, the CO overtone laser is not susceptible to water vapor as compared to a CO laser operating in the fundamental spectral region, excess water vapor can condense. This condensed liquid solution containing subject VOCs can change the characteristics of the VOCs and affect accurate testing of the sample.

It also may be advantageous to remove other major constituents of expired breath, such as nitrogen, oxygen and carbon dioxide. This can be accomplished by including an appropriate absorber 50 for the removal of one or more of these other constituents that are unnecessary for analysis of the gaseous sample but may reduce the photoacoustic signal level.

Microphone 34 is designed to detect pressure changes within photoacoustic cell 14. The pressure changes result from the heating of specific gaseous constituents, i.e., biomarkers, that may be present in the sample of breath undergoing an analysis within interior cavity 31. These pressure changes in photoacoustic cell 14 result from the characteristic intense absorption by one or more of the biomarkers. Typically, a specific biomarker's characteristic intense absorption is a substantially increased absorption of the radiation generated at a specific frequency by laser 16 and directed through photoacoustic cell 14.

However, even when a biomarker indicative of lung cancer is present in the sample being analyzed, only a small portion of the radiation emitted from laser 16 is absorbed within photoacoustic cell 14. A photodetector 51 is employed to monitor the power of laser 16 within photoacoustic cell 14. Photodetector 51 is used to help compensate for changes detected by microphone 34 due to changes in the power of radiation generated by laser 16.

In the embodiment illustrated, microphone 34 is coupled to an amplifier 52 preferably via a preamplifier 54 which receives a signal provide by microphone 34. Similarly, photodetector 51 is coupled to and provides a signal to an amplifier 56. The preamplifier 54/amplifier 52 combination detects and conditions microphone signals at the selected modulation frequency which optimizes the signal-to-noise ratio. Amplifiers 52 and 56 are preferably lock-in amplifiers that provide synchronous detection and reduce the influence of extraneous effects, such as noise, on the measurement of both the pressure changes within photoacoustic cell 14 and the radiation generated by laser 16.

Also, the modulation of the radiation emitted by laser 16 is synchronized with the gating of amplifiers 52 and 56. This may be accomplished by providing a reference signal 58 from the modulation source (e.g., chopper 24, if used, or voltage modulated high voltage power supply 18). Reference signal 58 is directed to lock-in amplifiers 52 and 56 which are able to detect signals that are synchronous with the modulation (i.e., at the same modulation frequency, with or without a phase shift).

The amplified signals from amplifiers 52, 56 are directed to a ratiometer 60 that, in turn, provides an output signal which is effectively a measure of the ratio of the signal detected by microphone 34 divided by the signal detected by photodetector 51. In other words, the signal is a measure of the fraction of the total input i radiation that is absorbed by a given biomarker or biomarkers within photoacoustic cell 14. This signal may then be directed to a data acquisition, analysis and display system 62 that is able to record, process, analyze and/or display the ratioed photoacoustic signal, as would be understood by one of ordinary skill in the art. It should be noted that the signal provided by microphone 34 can be further enhanced by introducing an acoustic modifier, such as helium, into photoacoustic cell 14 along with the sample being analyzed and/or as part of the sample.

The above described system provides very sensitive measurements, and has the ability to detect the presence of constituents that may only appear within the sample in parts per billion by volume. However, photoacoustic detection system 10 also can accurately detect the concentration levels of constituents within the gaseous sample. This is important for some constituents where changes in concentration from a normal level serve as a biomarker for the presence of a biological condition, such as lung cancer or other disease.

The concentration or density of a specific constituent is determined by measuring the signal strength of the signal detected by microphone 34 and comparing this to the signal strength(s) of a reference sample or samples of known concentration(s), as is understood in the art. Photoacoustic cell 14 is first calibrated using a reference sample or samples to measure signal levels provided by microphone 34 for known concentrations of the subject constituent. Over a broad range of concentrations, the photoacoustic signal level is linearly related to the concentration of a given dilute constituent within a sample mixture containing the constituent plus the acoustic signal enhancer, if used, all at a fixed total pressure. The concentration or density of the subject constituent within the sample can then accurately and readily be determined based on comparing the signal strength of the acoustic wave created from the constituent's characteristic absorption to those of the reference sample or samples.

One exemplary implementation of the present invention provides a method for detecting lung cancer in an individual, and includes analysis of a sample of the individuals breath to detect one or more lung cancer biomarkers. The sample may, for example, be originally provided by the individual via blowing into a sample container, such as sample container 38. The sample then can be analyzed or sent, e.g., mailed, to a central processing location where it is obtained for analysis.

According to further aspects of the invention, a laser, such as a CO overtone laser, or other appropriate radiation source is selected to generate a radiation that undergoes the characteristic intense absorption by the biomarker of interest. The radiation is directed into the sample of breath, and a detector, such as microphone 34, detects whether the characteristic absorption of the radiation occurs.

Figure 3:
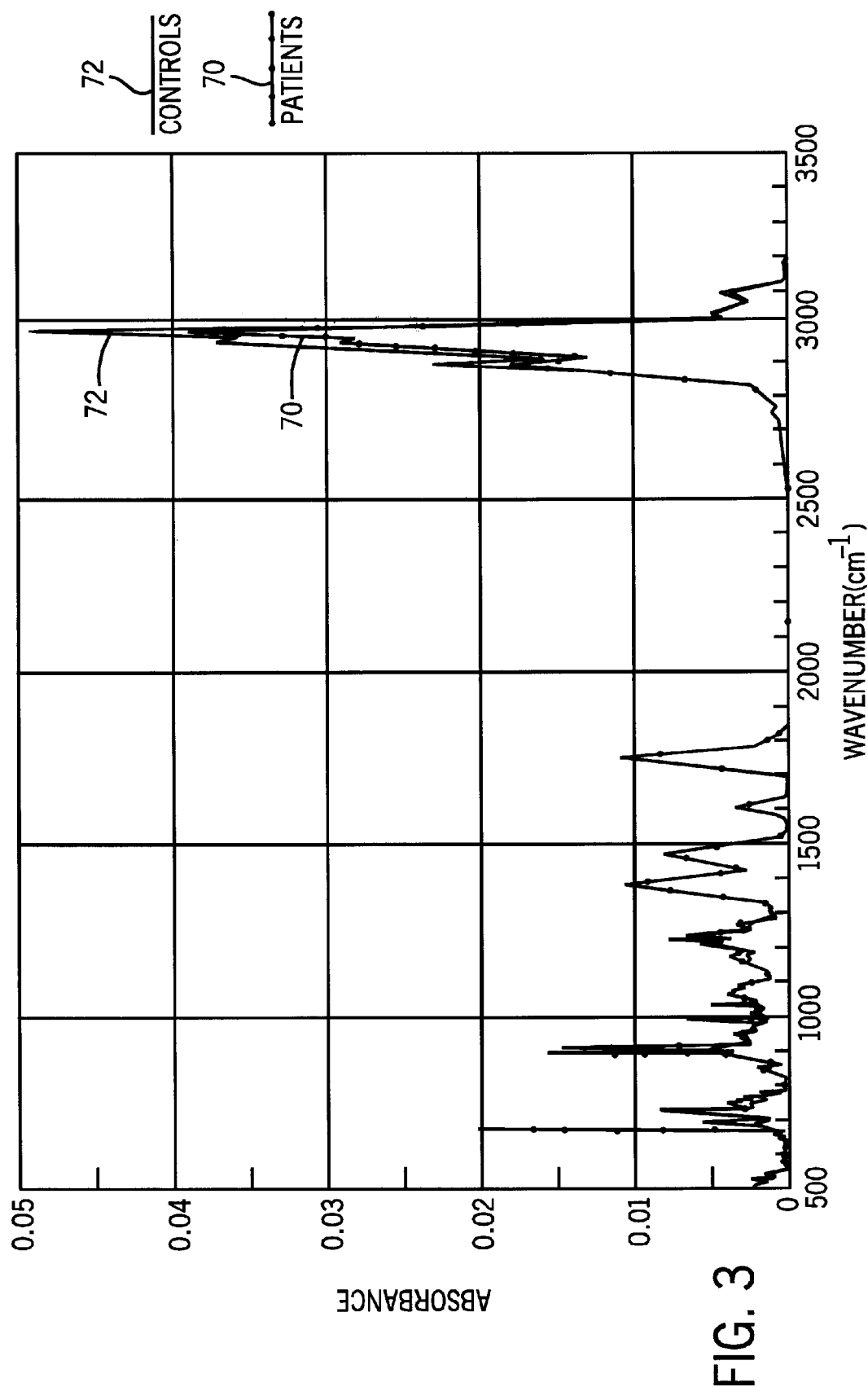
FIG. 3 is an infrared absorption spectra of breath samples of lung cancer patients compared to control subjects.

The present system and method are particularly amenable for use in screening patients for lung cancer. Research has shown that the breath samples of lung cancer patients differ from those of control subjects that do not have lung cancer. FIG. 3 illustrates an infrared absorption spectra of breath samples of lung cancer patients (shown by line 70) compared to control subjects (shown by line 72). These spectra are calculated from data on the mean abundances of the twenty most abundant VOCs found in breath samples. The data was established by a gas chromatographic/mass spectrometric study on 30 matched patients and 30 matched smoking controls, together with reference to infrared absorption spectra for these VOCS. The gas chromatograph/mass spectrometric study was done by H. J. O'Neill, Non-invasive Approach For Detection For Lung Cancer, final technical report, National Cancer Institute Grant No. CA 37056, IIT Research Institute, Chicago, Ill. 1990.

Figure 4:
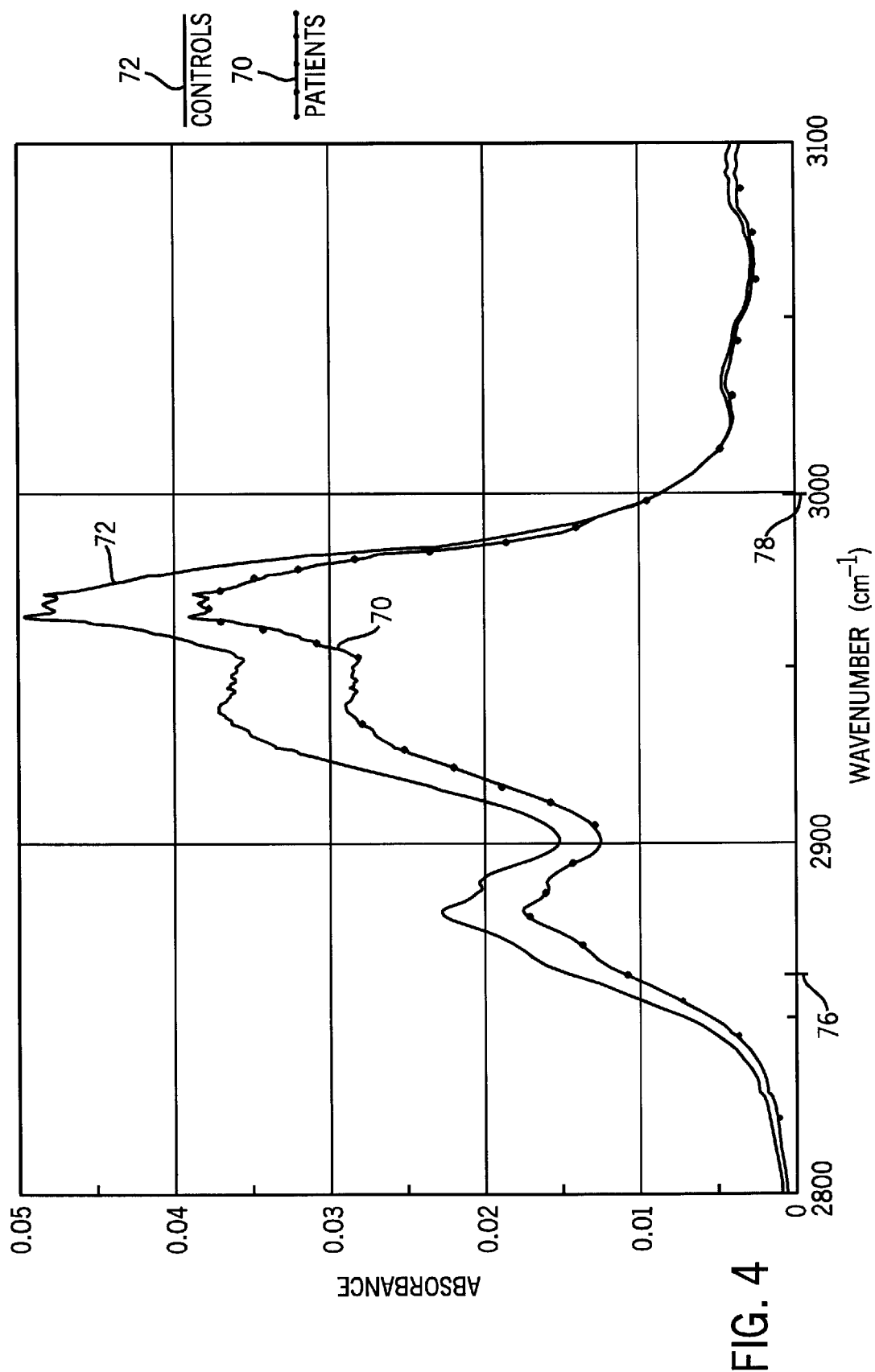
FIG. 4 is an expanded region of the infrared absorption spectra of FIG. 3.
Figure 5:
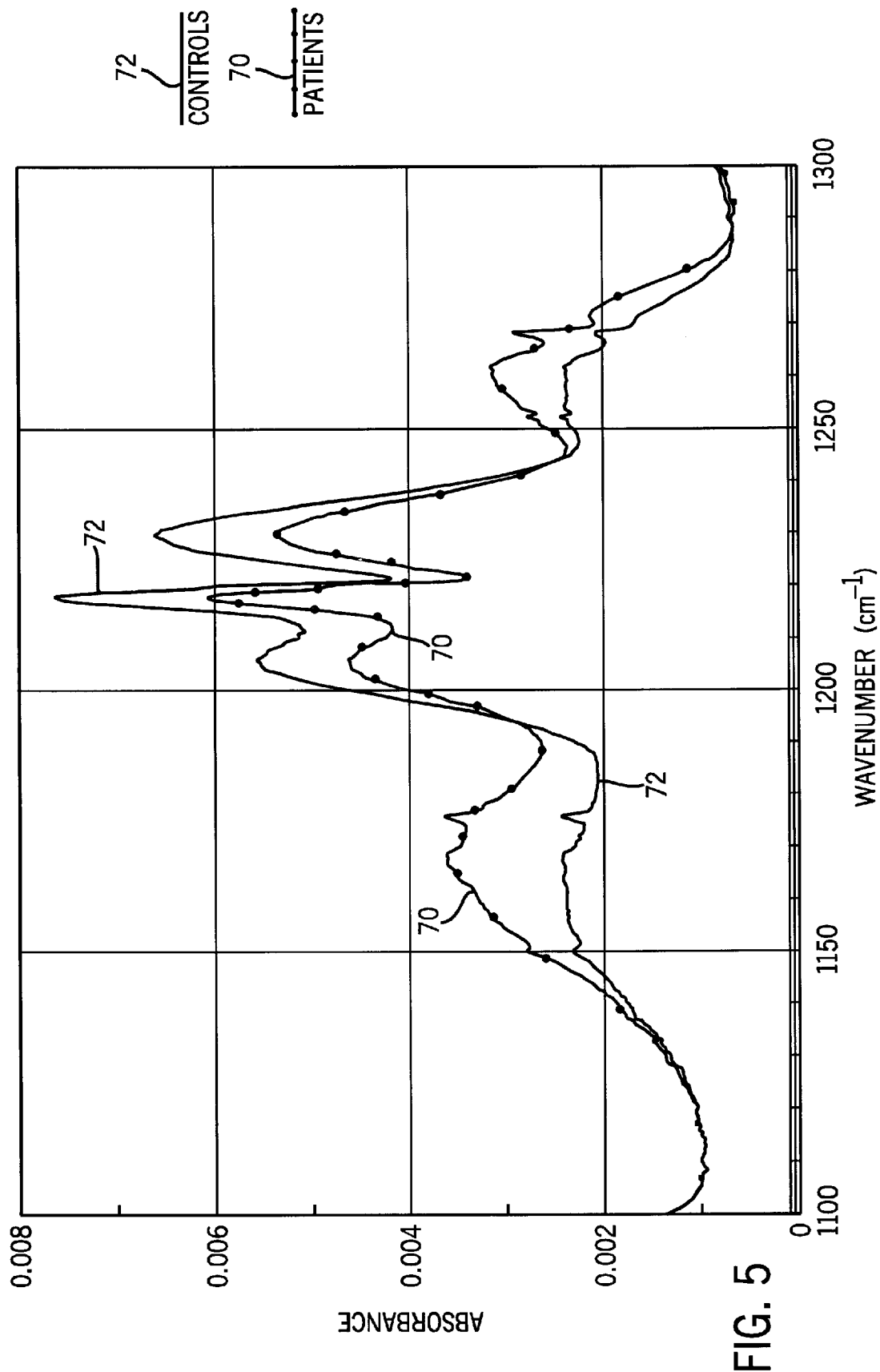
FIG. 5 is another expanded region of the infrared absorption spectra of FIG. 3.

FIGS. 4 and 5 show expanded regions of FIG. 3. In particular, FIG. 4 illustrates the expanded CH stretch absorption region (2800 to 3100 $cm^{-1}$). FIG. 5 illustrates the expanded CC stretch absorption region (1100 to 1300 $cm^{-1}$) for ketones, such as acetone and 2-butanone. As evident from both FIGS. 4 and 5, there are prominent differences between patient and control spectra in the two expanded regions. In FIGS. 3–5, the absorption spectra are illustrated graphically by plotting the level of absorbance along the vertical axis at a given wavenumber, plotted along the horizontal axis.

Laser photoacoustic detection, as described above, can be utilized in screening for lung cancer through measurement of absorbance of a given breath sample at a specific wavenumber or wavenumbers. The level of absorbance provides a strong indicator of the presence of lung cancer in the individual. A similar approach can be used in testing the breath sample for a variety of other biological conditions based on differences in the infrared absorption spectra of an individual with a specific condition relative to an individual that does not have the specific condition.

For example, the CO overtone laser, discussed above, works well in measuring the collective absorbance of the VOCs in a breath sample in the CH stretch absorption region where the wavenumber is approximately 2800 to 3100 $cm^{-1}$ (see FIG. 4). The differences between lung cancer patient breath samples and breath samples of controls in FIG. 4 are emphasized by calculating the ratio between patient and control absorption features, as illustrated by the graph 74 of FIG. 6. The CO overtone laser can readily be used in this region to accurately test the absorption of breath samples without incurring detrimental interference associated with the water vapor in breath.

Figure 6:
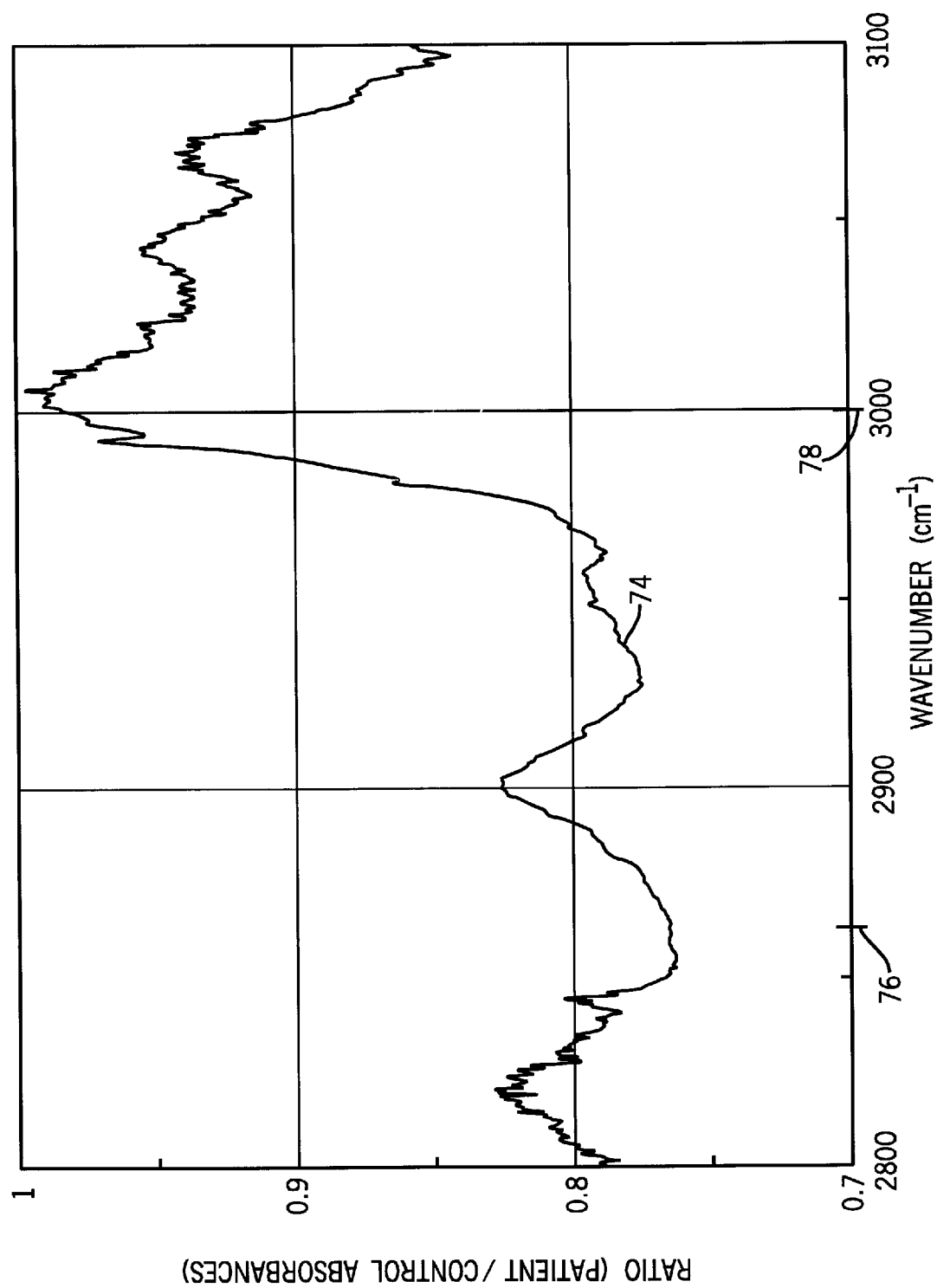
FIG. 6 is a graph showing the ratio between the patient and control absorption features in FIG. 4.

An exemplary test includes testing the level of absorption at the approximate wavenumber 2860 (marked by reference numeral 76 in FIGS. 4 and 6) and at the approximate wavenumber 3000 (as indicated by reference numeral 78 in FIGS. 4 and 6). The level of collective absorption serves as a biomarker indicative of a condition such as lung cancer. Also, the use of two points 76 and 78 can be helpful because they are at substantially diverse ratio points, as indicated in FIG. 6. Reference 76, at approximately wavenumber 2860, has a ratio value of approximately 0.77 which is at or towards the lowest ratio level in this spectral region. On the other hand, reference 78 has a ratio of nearly 1.0 which is near or at the highest ratio value in this particular spectral region. The absorption of a given patient's breath sample can be tested at wavenumbers corresponding to reference 76 and 78 to determine whether similar ratios (relative to the control graph 72) exist to indicate a likelihood of lung cancer. It should be noted that a wide variety of one or more points of comparison along the wavenumber axis can be utilized in optimizing the predictability of lung cancer or other biological conditions.

For example, as illustrated in FIG. 5, there may be other spectral regions that can provide an indication of a biological condition, such as lung cancer. FIG. 5 illustrates the absorbance of lung cancer patients and smoking controls in the 1100 to 1300 $cm^{-1}$ spectral region. Analysis of this region can be performed by, for example, a fundamental CO laser with fundamental ($\Delta v=-1$) laser transitions that occur in the approximately 8.0 to 9.0 $\mu$m spectral region. Analysis in this spectral region can be performed with long wavelength operation of the fundamental CO ($\Delta v=-1$) laser, because the absorption of water is minimal in this region. By staying outside of water absorption regions, a fundamental CO laser can be utilized as an appropriate energy generator. In fact, the clear crossover of patient graph line 70 and control graph line 72 at multiple points provides a series of areas/wavenumbers that can be utilized in analyzing a given breath sample to provide a strong indicator of whether the subject has lung cancer.

In the exemplary embodiment, laser 16 is a carbon monoxide (CO) laser having great flexibility with respect to control over the wavenumber at which radiation is emitted. This concept may be clarified with reference to FIG. 7 which includes a chart showing the relative laser gain coefficients for individual rotational lines within lasing vibrational bands V=30→28 through V=24→22 of the $^{12}C^{16}O$ overtone laser ($\Delta v=-2$). Each band consists of several CO laser transitions spaced ca 4 $cm^{-1}$ apart. The actual transitions that lase depend on gas partial pressures and electrical discharge conditions in the CO overtone laser.

Figure 7:
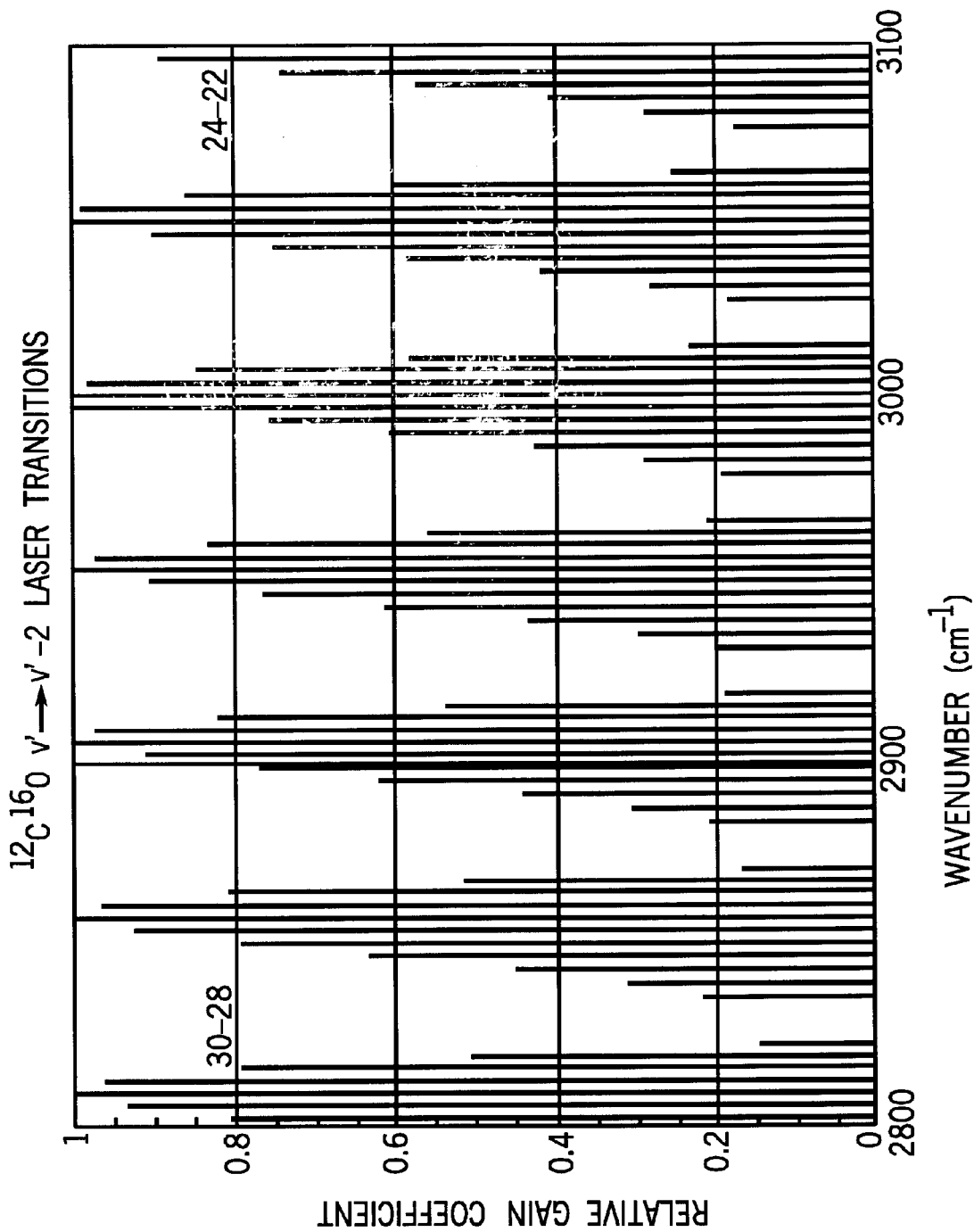
FIG. 7 is a graph of several exemplary bands of $^{12}C^{16}O$ (v→v-2) laser transitions in the CH stretch absorption region that may be used to obtain desired characteristic absorptions.

As illustrated by the chart, selection of the appropriate vibrational band and rotational line or lines within that band permits great control over the wavenumber of radiation emitted from laser 16. Although, FIG. 7 is based on the $^{12}C^{16}O$ isotope of carbon monoxide, numerous adjustments to the position of the laser lines within a given vibrational band, and consequently the wavenumber of the radiation emitted, can be made by choosing other isotopic variants of carbon monoxide (e.g. $^{13}C^{16}O$ or $^{12}C^{18}O$). This permits laser 16 to be accurately tuned to emit radiation having a desired wavenumber for absorption by a biomarker even if the characteristic intense absorption of that biomarker is spread over a small range of wavenumbers or fractions of wavenumbers.

With certain diseases or other biological conditions, there may be interference between the absorption spectra of biomarkers and other constituents within the gaseous sample. Sometimes, the interfering constituents can be removed from the sample prior to analysis by, for example, desiccants or absorbents. However, the interfering constituents are not always amenable to early removal.

In these situations, it may be necessary to determine the photoacoustic signal contributions of each of the interfering gases within the sample. This is particularly true when there are specific VOCs that serve as biomarkers, and other constituents interfere with biomarker detection. The gases of interest will tend to have interfering absorption spectra over a definite range of wavenumbers, and the actual gases involved can be determined from the various known absorption spectra of the constituents found in exhaled breath or other gaseous sample.

To determine the photoacoustic signal contributions of the interfering gases, laser 16 is adjusted to emit radiation having a predetermined wavenumber. The radiation is directed through photoacoustic cell 14 and the photoacoustic signal is measured. This procedure is repeated at different predetermined wavenumbers. The number of wavenumbers should be at least one greater than the sum of the number of biomarkers plus the number of interfering gases whose photoacoustic signal contributions are of interest. Preferably, the predetermined wavenumbers of the radiation are chosen for strong absorption by each of the different gaseous constituents of interest. The overall photoacoustic signal measured for each radiation having a given wavenumber can be treated as the linear sum of photoacoustic signal contributions by each relevant constituent of the sample. This can be described in algebraic form as follows:

$$S_j = \sum_{i=1}^{n} s_{ij}$$

$S_j$=the total photoacoustic signal provided by the mixture at a radiation having a given wavenumber j n=the number of constituents i in the mixture $S_{ij}$=the photoacoustic signal contribution for a particular constituent i, i.e. gas, at a particular wavenumber j Each photoacoustic signal contribution $S_{ij}$ of constituent i at wavenumber j is the product of a concentration for that constituent $c_i$ times its signal contribution at wavenumber j per unit concentration $\sigma_{ij}$.

$$S_{ij}=C_i\sigma_{ij}$$

The quantity $\sigma_{ij}$ is termed the "normalized photoacoustic signal contribution". The normalized photoacoustic signal contribution for each constituent i at each wavenumber j can be determined by measuring photoacoustic spectra (i.e., photoacoustic signals as a function of wavenumber) of reference samples of each constituent.

The concentrations of each of the constituents $c_i$ can be determined by, for example, least squares minimization of the residuals of calculated vs. measured total photoacoustic signal measurements $S_j$ as a function of trial value $c_i$. The calculations are typically performed on a processor or computer incorporated into unit 62 of photoacoustic system 10. By this method, the density or concentration of the constituents can be used to determine whether a biomarker indicative of a particular disease is present. If multiple interfering biomarkers are potentially present, this type of analysis also can be used to determine the concentrations of those multiple biomarkers.

It will be understood that the foregoing description is of preferred exemplary embodiments of this invention and that the invention is not limited to the specific forms shown. For example, a variety of photoacoustic cell designed may be use; a variety of data acquisition, processing and/or display units may be incorporated into the system; and the radiation source as well as the overall system may be adapted to screen for various biomarkers indicative of a wide variety of biological conditions, including food contamination, lung cancer and other diseases that produce volatile organic compounds in a given concentration that serve as a biomarker. These and other modifications may be made in the design and arrangement of the elements without departing from the scope of the invention as expressed in the appended claims.

What is claimed is:

1. A system for detecting a biomarker indicative of the presence of a biological condition, comprising:

a photoacoustic cell having an inlet through which a gaseous sample may be introduced into an interior of the photoacoustic cell;

an overtone laser combined with the photoacoustic cell, the overtone laser being positioned to direct a radiation through the photoacoustic cell, the radiation being of a frequency predetermined for a characteristic intense absorption by at least one specific biomarker contained in the gaseous sample, wherein the overtone laser comprises a CO overtone laser; and a detection system coupled to the photoacoustic cell to detect the characteristic intense absorption indicative of the at least one specific biomarker.

2. The system as recited in claim 1, wherein the overtone laser includes an optical cavity and the photoacoustic cell is disposed within the optical cavity.

3. A system for detecting a biomarker indicative of the presence of a biological condition, comprising:

a photoacoustic cell having an inlet through which a gaseous sample may be introduced into an interior of the photoacoustic cell;

an overtone laser combined with the photoacoustic cell, the overtone laser being positioned to direct a radiation through the photoacoustic cell, the radiation being of a frequency predetermined for a characteristic intense absorption by at least one specific biomarker contained in the gaseous sample, wherein the overtone laser uses CO overtone laser transitions based on $\Delta v=-2$ overtone band sequence; and a detection system coupled to the photoacoustic cell to detect the characteristic intense absorption indicative of the at least one specific biomarker.

4. The system as recited in claim 1, wherein the detection system comprises a microphone.

5. The system as recited in claim 1, further comprising an acoustic signal enhancer.

6. The system as recited in claim 1, wherein the biomarker comprises a volatile organic compound present in the gaseous sample.

7. The system as recited in claim 6, wherein the volatile organic compound is an indicator of lung cancer.

8. The system as recited in claim 3, wherein the biomarker comprises a volatile organic compound present in the gaseous sample.

9. The system as recited in claim wherein 8, the volatile organic compound is an indicator of lung cancer.

10. The system as recited in claim 3, wherein the overtone laser includes an optical activity and the photoacoustic cell is disposed within the optical cavity.

11. The system as recited in claim 3, wherein the detection system comprises a microphone.

12. The system as recited in claim 3, further comprising an acoustic signal enchancer.

* * * * *